(12) United States Patent
Zhang et al.

(10) Patent No.: US 12,144,554 B2
(45) Date of Patent: Nov. 19, 2024

(54) DISPLAY METHOD AND SYSTEM FOR ULTRASOUND-GUIDED INTERVENTION

(71) Applicants: SHENZHEN MINDRAY BIO-MEDICAL ELECTRONICS CO., LTD., Guangdong (CN); THE FIRST AFFILIATED HOSPITAL OF SUN YAT-SEN UNIVERSITY, Guangdong (CN)

(72) Inventors: Yanhui Zhang, Shenzhen (CN); Longfei Cong, Shenzhen (CN); Xiaoyan Xie, Guangzhou (CN); Ming Xu, Guangzhou (CN); Guangliang Huang, Guangzhou (CN); Xiaoer Zhang, Guangzhou (CN)

(73) Assignees: Shenzhen Mindray Bio-Medical Electronics Co., Ltd., Shenzhen (CN); The First Affiliated-Hospital of Sun Yat-Sen University, Guangzhou (CN)

( * ) Notice: Subject to any disclaimer, the term of this patent is extended or adjusted under 35 U.S.C. 154(b) by 1135 days.

(21) Appl. No.: 16/991,280

(22) Filed: Aug. 12, 2020

(65) Prior Publication Data
US 2020/0367972 A1  Nov. 26, 2020

Related U.S. Application Data

(63) Continuation of application No. PCT/CN2018/076534, filed on Feb. 12, 2018.

(51) Int. Cl.
*A61B 5/00* (2006.01)
*A61B 34/10* (2016.01)
*A61B 90/00* (2016.01)

(52) U.S. Cl.
CPC .............. *A61B 34/10* (2016.02); *A61B 90/37* (2016.02); *A61B 2034/104* (2016.02);
(Continued)

(58) Field of Classification Search
CPC .............. A61B 34/10; A61B 2034/37; A61B 2034/107; A61B 2090/378; A61B 2090/3925
See application file for complete search history.

(56) References Cited

U.S. PATENT DOCUMENTS

| 2005/0033160 | A1* | 2/2005 | Yamagata | A61B 6/12 600/425 |
| 2016/0324584 | A1 | 11/2016 | Maraghoosh et al. | |
| 2017/0303892 | A1 | 10/2017 | Antol et al. | |

FOREIGN PATENT DOCUMENTS

| CN | 102846337 A | 1/2013 |
| CN | 105534593 A | 5/2016 |

(Continued)

OTHER PUBLICATIONS

PCT International Search Report and the Written Opinion mailed Aug. 9, 2018, issued in related International Application No. PCT/CN2018/076534, with partial English translation (8 pages).

(Continued)

*Primary Examiner* — Joel F Brutus
(74) *Attorney, Agent, or Firm* — Sheppard Mullin Richter & Hampton LLP

(57) ABSTRACT

A display method and system for ultrasound-guided intervention. The method comprises: obtaining, via a probe, a data, wherein the data comprises at least a real-time ultrasound data and a real-time spatial orientation information of the probe; obtaining, by a processor, an ablation needle plan, wherein, the ablation needle plan comprises at least a probe marker for planning, a needle insertion path and a predicted ablation area corresponding to the needle insertion path, and the probe marker for planning is generated in a form that is able to indicate one side or multiple sides of the probe such that an orientation of the probe marker for planning represents a planned orientation of the probe; generating, by the (Continued)

---

Obtain a data, where the data includes at least a three-dimensional data, a real-time ultrasound data and a real-time three-dimensional spatial position information of a probe

S10

Generate and display a planning image, where, the planning image includes a probe marker for planning, an ultrasound image and an area of tissue to be ablated and represent at least a relative spatial position relationship of the probe marker, the ultrasound image and the area of tissue to be ablated, and the probe marker is generated and displayed in a form that is able to indicate one or multiple orientations of the probe

S12 processor, a guiding image for ultrasound-guided intervention according to the obtained data and the ablation needle plan; and displaying, by a display device, the guiding image.

20 Claims, 6 Drawing Sheets

(52) U.S. Cl.
CPC ... *A61B 2034/107* (2016.02); *A61B 2090/378* (2016.02); *A61B 2090/3925* (2016.02)

(56) References Cited

FOREIGN PATENT DOCUMENTS

| | | | |
|---|---|---|---|
| CN | 105899143 | A | 8/2016 |
| CN | 107072632 | A | 8/2017 |
| JP | 2004057379 | A | 2/2004 |
| WO | 2015-092628 | A1 | 6/2015 |

OTHER PUBLICATIONS

First Search dated Aug. 11, 2021, issued in related Chinese Application No. 201880057453.4 (2 pages).
Supplementary Search dated Apr. 27, 2022, issued in related Chinese Application No. 201880057453.4 (3 pages).

* cited by examiner

```
┌─────────────────────────────────────────────────────────────────┐
│ Obtain a data, where the data includes at least a three-dimensional data, a real-time │
│ ultrasound data and a real-time three-dimensional spatial position information of a │
│                              probe                              │
└─────────────────────────────────────────────────────────────────┘
                                    │
                                    │        S10
                                    ▼
┌─────────────────────────────────────────────────────────────────┐
│ Generate and display a planning image, where, the planning image includes a probe │
│   marker for planning, an ultrasound image and an area of tissue to be ablated and │
│   represent at least a relative spatial position relationship of the probe marker, the │
│     ultrasound image and the area of tissue to be ablated, and the probe marker is │
│ generated and displayed in a form that is able to indicate one or multiple orientations │
│                            of the probe                         │
└─────────────────────────────────────────────────────────────────┘
                                            S12
```

FIG. 1

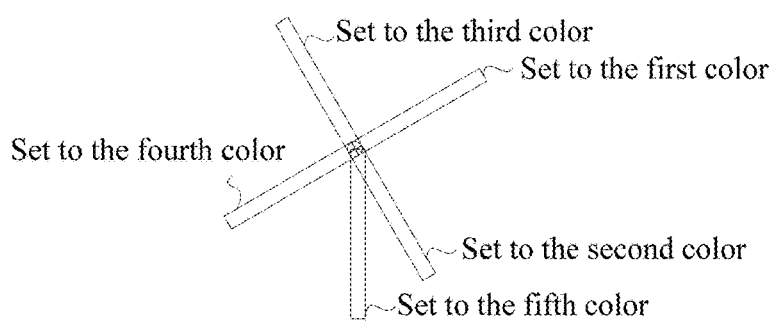

FIG. 2

```
┌─────────────────────────────────────────────────────────────────┐
│ Obtain a data, where the data includes at least a three-dimensional data, a real-time │
│ ultrasound data and a real-time three-dimensional spatial position information of a   │
│                               probe                                                    │
└─────────────────────────────────────────────────────────────────┘
                                    │
                                    │   S20
                                    ▼
┌─────────────────────────────────────────────────────────────────┐
│ Generate and display a guiding image for ultrasound-guided intervention according │
│ to the obtained data and a pre-saved ablation needle plan, where, the guiding image │
│  includes a probe marker for planning, a probe marker for guiding, an ultrasound    │
│    image and an area of tissue to be ablated and represent at least a relative spatial │
│   position relationship between the probe marker for planning, the probe marker for │
│    guiding, the ultrasound image and the area of tissue to be ablated, and the probe │
│    marker is generated and displayed in a form that is able to indicate one or multiple │
│                         orientations of the probe                                      │
└─────────────────────────────────────────────────────────────────┘
                                                                    S22
```

FIG. 7

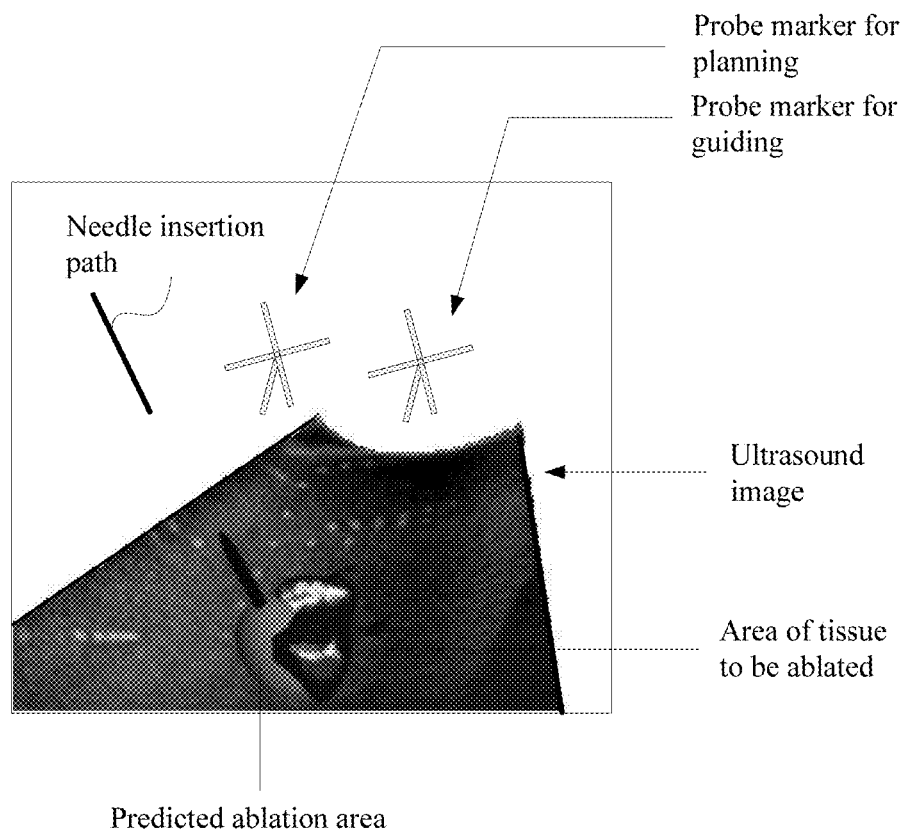

FIG. 8

DISPLAY METHOD AND SYSTEM FOR ULTRASOUND-GUIDED INTERVENTION

CROSS-REFERENCE TO RELATED APPLICATION

The application is a continuation application of International Patent Application No. PCT/CN2018/076534, filed with the China National Intellectual Property Administration (CNIPA) on Feb. 12, 2018, and entitled "DISPLAY METHOD AND SYSTEM FOR ULTRASOUND-GUIDED INTERVENTION". The entire content of the above-identified application is incorporated herein by reference.

TECHNICAL FIELD

The present disclosure relates to ultrasound-guided intervention, in particular to display methods and systems for ultrasound-guided intervention.

BACKGROUND

Ultrasound-guided intervention technology, as a branch of modern ultrasound medicine, was officially confirmed at the World Interventional Ultrasound Academic Conference held in Copenhagen in 1983. Ultrasound-guided intervention technology is developed on the basis of ultrasound imaging so as to further meet the needs of clinical diagnosis and treatment. The main concept thereof is to complete various operations such as biopsy, X-ray contrast imaging, aspiration, intubation and medicine injection, etc., under the monitoring or guidance of real time ultrasound imaging, so as to avoid certain surgical operations and achieve results comparable to surgical operations.

A major application of the ultrasound-guided intervention technology is to assist the ablation surgery. Specifically, the ultrasound-guided intervention technology can assist the user (such as the surgeon) to perform the preoperative planning and the intraoperative guidance. The preoperative planning may refer to acquiring enhanced three-dimensional data (which will not be limited to CT/MRI and ultrasound image data) of the patient's lesion area and then make a surgical plan (including the number of ablation needles, the needle insertion paths, the ablation power or other parameters) on the three-dimensional data before the formal ablation operation. The advantage of the preoperative planning is that the best surgical plan can be made in advance so as to avoid the blindness of the needle. The intraoperative guidance may refer to guiding the user to perform the operation according to the best plan obtained in the preoperative planning utilizing the real-time characteristics of the ultrasound imaging so as to maximize the success rate of the ablation surgery.

The preoperative planning and the intraoperative guidance may be collectively referred to as planning guidance, which may generally include two categories. One is based on enhanced CT/MRI images, and the other is based on contrast enhanced ultrasound (CEUS) image. Both methods have their own advantages and disadvantages.

The planning guidance technology based on the enhanced CT/MRI images may have the advantages of high resolution, wide field of view and being able to clearly observe the lesion area, the important blood vessels in the liver, the ribs, the lungs, the stomach and other organs and tissues that may affect the ablation surgery. Specifically, the planning guidance based on the enhanced CT/MRI images is offline, that is, the planning operation does not need to be performed on the operating table and the user can make the ablation plan anytime and anywhere, which is convenient and flexible. The disadvantage of the planning guidance based on the enhanced CT/MRI images is that the long delay may cause inconsistency between the planning and the guidance, that is, the relative positional relationship between the organs when they are scanned to obtain the enhanced CT/MRI data may be different from the relative positional relationship between the organs when the ablation surgery is performed. For example, the states of the gallbladder and hepatic blood vessels when the patient is hungry and full are very different, and the change of the shape of the stomach may also deform the liver. These influencing factors seem to be minimal. However, because the liver tumors are often small with respect to these organs, even slight changes in blood vessel morphology may directly affect the registration accuracy of the CT/MRI images with the ultrasound images, thereby causing deviations between the tumor area identification in the three-dimensional data and the actual tumor area. Therefore, the previously planned plan cannot be mapped to the actual tumor area correctly, which will affect the accuracy of the ablation operation.

The planning guidance based on the CEUS images may overcome the shortcomings of the above-mentioned planning guidance based on the enhanced CT/MRI images. In the CEUS image-based planning guidance, the preoperative planning may be performed on the three-dimensional contrast enhanced ultrasound image data which can be obtained more easily than the CT/MRI data. By the scanning with a volume probe or the sector scanning with a convex probe, the three-dimensional contrast enhanced ultrasound image data can be obtained within a few minutes. The user can perform the ablation surgery without moving the bed after planning a plan on the three-dimensional data. With this method, the planning and guidance cycle can be greatly shortened and the impact of vascular deformation can be minimized. At the same time, the use of magnetic navigation technology can simplify the pre-operative operation process and facilitate the user's operation greatly while ensuring the registration accuracy. However, compared with the planning guidance technology based on enhanced CT/MRI images, the disadvantage of the planning guidance technology based on CEUS images is that the field of view is limited, and due to the characteristics of ultrasound imaging, the ribs and lungs cannot be displayed on the image. Therefore, the planning of the plan needs to be performed online in real time in order to avoid the obstruction of the needle insertion path by ribs, blood vessels or other important organs.

SUMMARY

The present disclosure provides display methods and systems for ultrasound-guided intervention.

In one embodiment, a display method for ultrasound-guided intervention is provided, which may include: obtaining a data, where the data includes at least a real-time ultrasound data and a real-time spatial orientation information of a probe; generating and displaying a planning image for the ultrasound-guided intervention according to the obtained real-time ultrasound data and the real-time spatial orientation information of the probe, where, the planning image may include a probe marker for planning, an ultrasound image and an area of tissue to be ablated and represent at least a relative spatial position relationship of the probe marker, the ultrasound image and the area of tissue to be ablated, and the probe marker may be generated and displayed in a form that is able to indicate one or multiple sides of the probe.

In one embodiment, a display method for ultrasound-guided intervention is provided, which may include: obtaining a data, where the data includes at least a real-time ultrasound data and a real-time spatial orientation information of a probe; generating and displaying a guiding image for ultrasound-guided intervention according to the obtained real-time ultrasound data, the obtained real-time spatial orientation information of the probe and a pre-saved ablation needle plan, where, the guiding image may include a probe marker for planning, a probe marker for guiding, an ultrasound image and an area of tissue to be ablated and represent at least a relative spatial position relationship between the probe marker for planning, the probe marker for guiding, the ultrasound image and the area of tissue to be ablated, the probe marker for planning in the guiding image may be used to assist a user to coincide the probe marker for guiding with the probe marker for planning by moving a probe, and the probe marker may be generated and displayed in a form that is able to indicate one or multiple sides of the probe.

In one embodiment, the one orientation of the probe may be any one of a front of the probe, a back of the probe, a left of the probe and a right of the probe, and the multiple sides of the probe may be at least two of the front of the probe, the back of the probe, the left of the probe and the right of the probe. Alternatively, the multiple sides of the probe may be at least two or at least three of the front of the probe, the back of the probe, the left of the probe, the right of the probe and the transmitting side of the probe, where the at least three orientations may include the transmitting side of the probe.

In one embodiment, the probe marker may include one or multiple linear objects. The number of the linear objects may be equal to the number of the sides of the probe indicated by the probe marker, and each linear object may indicate one side of the probe. In the case that there are multiple linear objects, the linear objects may be different in a first-type attribute. The first-type attribute may include a color, a length and/or a thickness. Alternatively, different marks may be marked on the linear objects. The marks may include a Chinese abbreviation or an English initial of the side of the probe indicated by the linear object. Alternatively, the probe marker may include a probe model and one or multiple arrows arranged around the probe model. Each arrow may indicate one side of the probe. In the case that there are multiple arrows, the arrows may be different in a first-type attribute. The first-type attribute may include a color, a length and/or a thickness. Alternatively, different marks may be marked on the arrows. The marks may include a Chinese abbreviation or an English initial of the side of the probe indicated by the arrow.

In one embodiment, the probe marker for planning and the probe marker for guiding may be different in a second-type attribute. The second-type attribute may include a brightness and/or a transparency. Alternatively, different marks may be marked on the probe marker for planning and the probe marker for guiding.

In one embodiment, a display system for ultrasound-guided intervention is provided, which may include: a probe; a transmitting/receiving control circuit which is configured to control the probe to scan a tissue to obtain a real-time ultrasound data; a positioning device which is configured to obtain a real-time spatial orientation information of the probe; a processor which is configured to generate a planning image for ultrasound-guided intervention according to the obtained real-time ultrasound data and the real-time spatial orientation information of the probe, where, the planning image comprises a probe marker for planning, an ultrasound image and an area of tissue to be ablated and represents at least a relative spatial position relationship of the probe marker, the ultrasound image and the area of tissue to be ablated, and the probe marker is generated and displayed in a form that is able to indicate one or multiple sides of the probe; and a display device which is configured to display the planned image for ultrasound-guided intervention.

In one embodiment, a display system for ultrasound-guided intervention is provided, which may include: a probe; a transmitting/receiving control circuit which is configured to control the probe to scan a tissue to obtain a real-time ultrasound data; a positioning device which is configured to obtain a real-time spatial orientation information of the probe; a processor which is configure to generate a guiding image for ultrasound-guided intervention according to the obtained real-time ultrasound data, the obtained real-time spatial orientation information of the probe and a pre-saved ablation needle plan, where, the guiding image comprises a probe marker for planning, a probe marker for guiding, an ultrasound image and an area of tissue to be ablated and represents at least a relative spatial position relationship between the probe marker for planning, the probe marker for guiding, the ultrasound image and the area of tissue to be ablated, the probe marker for planning in the guiding image is used to assist a user to coincide the probe marker for guiding with the probe marker for planning by moving a probe, and the probe marker is generated and displayed in a form that is able to indicate one or multiple sides of the probe; and a display device which is configured to display the guiding image for ultrasound-guided intervention.

In one embodiment, the probe marker generated by the processor and displayed by the display device may indicate one side of the probe which is any one of a front of the probe, a back of the probe, a left of the probe and a right of the probe or indicate multiple sides of the probe which are at least two of a front of the probe, a back of the probe, a left of the probe and a right of the probe, or are at least two or at least three of a front of the probe, a back of the probe, a left of the probe, a right of the probe and a transmitting side of the probe. The at least three sides may include the transmitting side of the probe.

In one embodiment, the probe marker generated by the processor and displayed by the display device may include one or multiple linear objects. The number of the linear objects may be equal to the number of the sides of the probe indicated by the probe marker. Each linear object may indicate one side of the probe. In the case that there are multiple linear objects, the linear objects may be different in a first-type attribute. The first-type attribute may include a color, a length and/or a thickness. Alternatively, different marks may be marked on the linear objects. The marks may include a Chinese abbreviation or an English initial of the side of the probe indicated by the linear object. Alternatively, the probe marker may include a probe model and one or multiple arrows arranged around the probe model. Each arrow may indicate one side of the probe. In the case that there are multiple arrows, the arrows may be different in a first-type attribute. The first-type attribute may include a color, a length and/or a thickness. Alternatively, different marks may be marked on the arrows. The marks may include a Chinese abbreviation or an English initial of the side of the probe indicated by the arrow.

In one embodiment, the processor may be further configured to set the probe marker for planning and the probe marker for guiding with different second-type attribute. The second-type attribute may include a brightness and/or a transparency. Alternatively, the processor may mark the probe marker for planning and the probe marker for guiding with different marks.

With the display methods or systems for ultrasound-guided intervention in the embodiments, the planning image may be generated and displayed, by which the user can conveniently view the area of tissue to be ablated, the relative spatial positions of the ultrasound image and the area of tissue to be ablated, the needle insertion path and the predicted ablation area during preoperative planning. It not only provides a more intuitive display effect, but also provide the relative spatial positional relationship between the probe, the area of tissue to be ablated, the ultrasound image, the needle insertion path and the predicted ablation area, which can help the user to quickly and accurately locate the area of tissue to be ablated and complete the preoperative planning to make an interventional surgery plan. Furthermore, because the probe marker itself can represent the direction of the probe by indicating one or multiple sides of the probe, the spatial position of the probe relative to the area of tissue to be ablated and the current placement state of the probe (such as the direction of the probe and the location of the probe) can be clearly displayed by the planning image. Therefore, it can provide an effective reference in orientation relative to the probe during the following planning for needle insertion path in the planning stage.

With the display methods and systems for ultrasound-guided intervention provided in the embodiment, the guiding image may be generated and displayed, which may be used for assisting the user to perform the planned needle insertion and the ablation. The guiding image may include the probe marker for planning and the probe marker for guiding. By moving the probe, the user can make the probe marker for guiding to coincide with the probe marker for planning. Therefore, the needle insertion path in the planning stage can be accurately located, so as to ensure the intervention accuracy as much as possible, avoid the incomplete ablation of the area of tissue to be ablated, and reduce the normal tissue damage.

BRIEF DESCRIPTION OF THE DRAWINGS

FIG. 1 is a flowchart of a display method for ultrasound-guided intervention in one embodiment.

FIG. 2 schematically shows a probe marker in one embodiment.

FIG. 4(*b*) is a planning image generated in one embodiment, on which a needle insertion path and the corresponding predicted ablation area are displayed.

FIG. 7 is a flowchart of a display method for ultrasound-guided intervention in another embodiment.

FIG. 8 schematically shows a guiding image generated in one embodiment.

DETAILED DESCRIPTION

Figure 3:
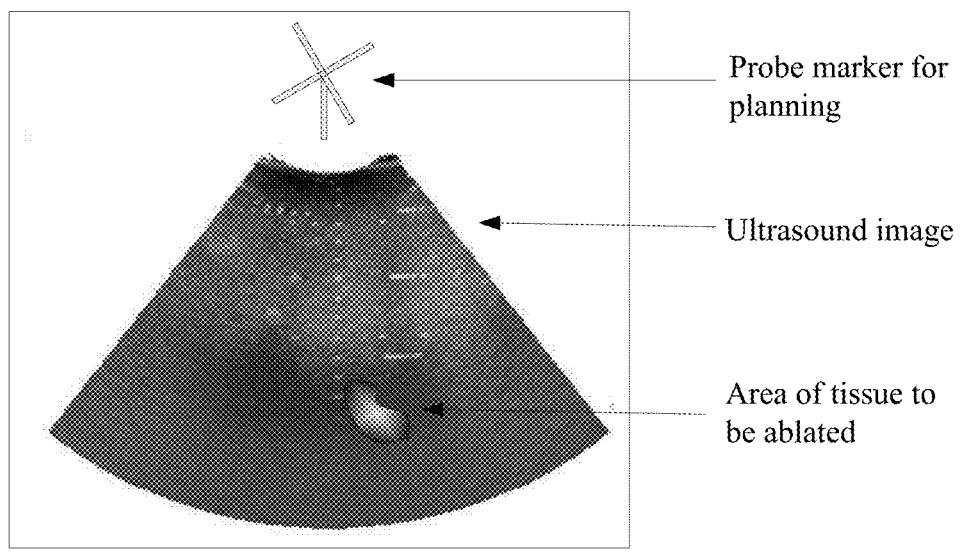
FIG. 3 schematically shows a planning image generated in one embodiment.

The present disclosure will be described in detail below through specific embodiments and drawings. In different embodiments, similar elements will be assigned with similar numbers. In the following embodiments, many details will be described such that the present disclosure can be better understood. However, those skilled in the art can easily recognize that some of the features may be omitted in different situations, or may be replaced by other elements, materials or methods. In some cases, some operations in the present disclosure will not be shown or described in the specification, which is to avoid the core part of the present disclosure being overwhelmed by too much description. For those skilled in the art, detailed description of these operations is not necessary. They can fully understand the operations according to the description in the specification and general technical knowledge in the field.

In addition, the features, operations or characteristics described in the specification may be combined in any appropriate manner to form various embodiments. Furthermore, the steps or actions in the described methods can also be replaced or adjusted in the execution order in a manner obvious to those skilled in the art. Therefore, the various orders in the specification and drawings are only for clearly describing a certain embodiment, but not meant to be a necessary order, unless otherwise stated that a certain order must be followed.

The serial numbers themselves, such as "first", "second", etc., are used to distinguish the described objects, but not have any order or technical meaning. The "connection" and "coupling" mentioned in the present disclosure, unless otherwise specified, will include direct and indirect connection (coupling).

Referring to FIG. 1, in one embodiment, a display method for ultrasound-guided intervention is disclosure, which may include step S10 and step S12. Detailed description will be provided below.

In step S10, data may be obtained. The data may at least include real-time ultrasound data and real-time spatial orientation information of the probe. The real-time ultrasound data may be two-dimensional or three-dimensional ultrasound data obtained by scanning the tissue by the probe, or other suitable real-time data representing the tissue. The real-time spatial orientation information of the probe may be obtained by a positioning device, such as an orientation sensor, etc. The real-time spatial orientation information may include the location information of the probe and the direction information of the probe.

In step S12, a planning image of ultrasound-guided intervention may be generated based on the obtained data and displayed. The planning image may include a probe marker for planning, an ultrasound image and an area of tissue to be ablated. The planning image may at least represent the relative spatial position relationship between the probe marker for planning, the ultrasound image and the area of tissue to be ablated. In one embodiment, in step S12, the ultrasound image may be generated according to the real time ultrasound data and displayed in real time; the area of tissue to be ablated may be obtained according to the obtained data, where the area of tissue to be ablated may be able to be displayed in a three-dimensional form in the planning image; and the area of tissue to be ablated may be displayed in the planning image. The area of tissue to be ablated may be displayed in a single color, that is, it may only present the size and shape of the tissue to be ablated, but ignore the attributes such as the internal density and gray value of the tissue to be ablated, etc., because in the planning image what are concerned may be the relative spatial position relationship between the probe marker for planning, the ultrasound image and the area of tissue to be ablated such that the user can understand the relative spatial position relationship between the actual probe, the tissue area represented by the ultrasound image and the area of tissue to be ablated. In addition, a real-time two-dimensional image for observing the area of tissue to be ablated may also be generated and displayed. In actual applications, a typical tissue to be ablated may be a tumor.

The probe marker included in the planning image may be generated and displayed in a form which is able to indicate one or more sides of the probe. When the probe marker is generated and displayed in a form that can indicate one side of the probe such that an orientation of the probe marker for planning represents a planned orientation of the probe. The orientation of the probe here may include the location of the probe and the direction of the probe, and the orientation of the probe marker for planning may include the location of the probe marker for planning and the direction of the probe marker for planning.

Said one side may be any one of the front side, the back side, the left side and the right side of the probe; when the probe marker is generated and displayed in a form that can indicate multiple sides of the probe, said multiple sides may be at least two of the front side, the back side, the left side and the right side of the probe, or at least two or three of the front side of the probe, the back side of the probe, the left side of the probe, the right side of the probe and the transmitting side of the probe, where "at least three sides" may include the transmitting side of the probe. The probe marker may be embodied in many specific forms. For example, in one embodiment, the probe marker may include one or multiple linear objects. The number of the linear objects may be equal to the number of the sides of probe to be indicated by the probe marker, and each linear object may indicate one side of the probe. In the case that there are multiple linear objects, the linear objects may be different in the first-type attribute. The first-type attribute may include the color, the length and/or the thickness. Alternatively, different marks may be marked on the linear objects. The marks may include the Chinese abbreviation or the English initial of the side of the probe indicated by the linear object. FIG. 2 shows a probe marker which includes five linear objects. Each linear object has a different color, and respectively represents one side of the probe. For example, the five linear objects may respectively represent the front side of the probe, the back side of the probe, the left side of the probe, the right side of the probe and the transmitting side of the probe. The probe marker may also be in other forms. For example, in one embodiment, the probe marker may include a probe model and one or more arrows arranged around the probe model, and each arrow may indicate one side of the probe. In the case that there are multiple arrows, the arrows may be different in a first-type attribute. The first-type attribute may include the color, the length and/or the thickness. Alternatively, different marks may be marked on the arrows. The marks may include the Chinese abbreviation or the English initial of the side of the probe indicated by the arrow. In one embodiment, the size of the probe marker may be zoomed in or out according to user needs, or be set to an initial default value. The probe marker disclosed in the present embodiment is very visually intuitive. Furthermore, because the probe marker itself can represent the direction of the probe by indicating one or more sides of the probe, the spatial orientation of the probe relative to the area of tissue to be ablated and the current placement state of the probe (such as the direction of the probe and the location of the probe) can be clearly displayed by the planning image. Therefore, it can provide an effective reference in orientation relative to the probe during the following planning for needle insertion path in the planning stage.

When the probe is moved, the planning image may also be updated accordingly. The update of the planning image may include update of the spatial orientation of the probe marker for planning, the spatial position of the ultrasound image and the image content of the ultrasound image in the planning image.

Through the step S10 and the step S30 above, the planning image may be generated and displayed. The planning image may be used to assist the user in preoperative planning. For example, FIG. 3 shows a planning image in which the probe marker shown in FIG. 2 is used.

Figure 4:
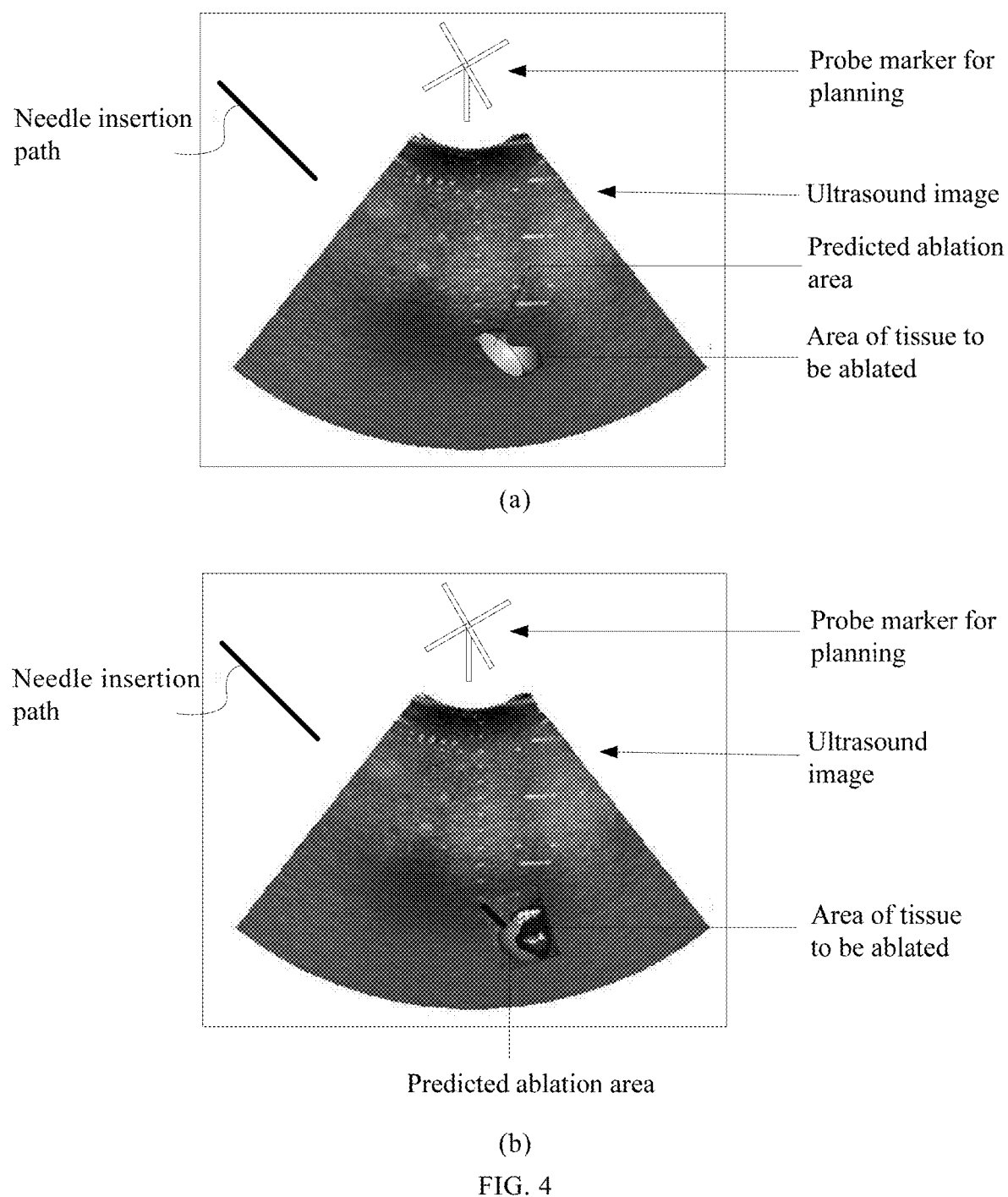
FIG. 4(*a*) is a planning image generated in one embodiment, on which a needle insertion path and the corresponding predicted ablation area are displayed.
Figure 5:
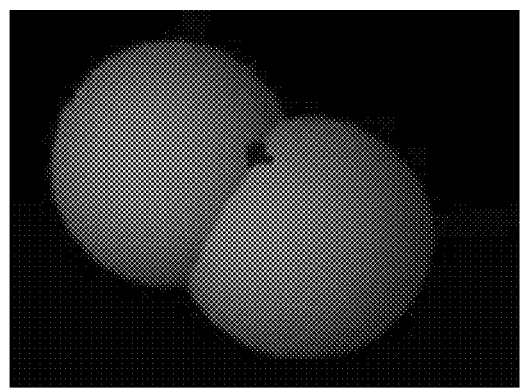
FIG. 5 schematically shows a predicted ablation area in one embodiment which is three dimensional and is displayed with a color different from that of the area of tissue to be ablated.

When performing a planning, the user can set the needle insertion path and the ablation parameters on the planning image according to the content of the planning image. For example, in one embodiment, the display method for ultrasound-guided intervention may further include the following steps: receiving an instruction for setting the needle insertion path and an instruction for setting the ablation parameters, and generating the needle insertion path of the ablation needle and the predicted ablation area on the planning image according to the two instructions. In the case that the area of tissue to be ablated displayed on the planning image is three-dimensional, the generated and displayed predicted ablation area may also be three-dimensional. When the instruction for setting the needle insertion path or the instruction for setting the ablation parameter is updated, the needle insertion path or the predicted ablation area generated on the planning image may also be updated accordingly. In one embodiment, in the case that there is overlap area between the predicted ablation area and the area of tissue to be ablated, the planning image will show the overlap between the predicted ablation area and the three-dimensional area of tissue to be ablated. FIG. 4(a) shows the planning image after receiving the instruction for setting the needle insertion path and the instruction for setting the ablation parameter. In one embodiment, the needle insertion path may be shown by a solid line, a dashed line or an arrow, etc. in a certain color. By the needle insertion path on the planning image, the user can clearly observe the organs and tissues to be punctured by the ablation needle when the ablation needle is inserted along the needle insertion path. Therefore, the accidental injury to important organs and blood vessels and the influence of ribs to the needle insertion path can be avoided during the planning of the needle insertion path. The predicted ablation area may simulate the predicted ablation range under the set needle insertion path and the set ablation parameter. Since the actual ablation range is usually ellipsoidal, in one embodiment, a three-dimensional ellipsoid may be used to represent the predicted ablation arrange. The transparency of the predicted ablation range displayed on the planning image may be adjustable, so as to facilitate the observation of the overlap between the predicted ablation area and the area of tissue to be ablated. When the predicted ablation area completely covers the area of tissue to be ablated, it means that the area of tissue to be ablated will be completely ablated. FIG. 4(b) shows the planning image where the area of tissue to be ablated is three-dimensional and the predicted ablation range is a three-dimensional ellipsoid. The overlap between the predicted ablation area and the three-dimensional area of tissue to be ablated can be clearly observed. It should be noted that when only one ablation needle is set, one predicted ablation area may completely cover the area of tissue to be ablated; when multiple ablation needle are set, multiple predicted ablation areas may together completely cover the area of tissue to be ablated. In one embodiment, the predicted ablation area and the area of tissue to be ablated may be displayed in different colors, so as to facilitate the user to observe the predicted ablation of the area of tissue to be ablated. Therefore, it will be easy to observe the small areas which will be prone to be missed when observed in traditional two-dimensional images layer by layer, thereby effectively improving the success rate of ablation surgery. For example, FIG. 5 shows a small area of the missed area of tissue to be ablated which can be easily observed in the planning image when there are two predicted ablation areas. In the figure, the two three-dimensional ellipses are the two predicted ablation areas. There is a dark area at the boundary between them, which is the small area in the missed area of tissue to be ablated.

When a save instruction is received, at least the current needle insertion path, the predicted ablation area, the probe marker for planning and the ablation parameters on the current planning image, as well as the relative spatial position relationship between the needle insertion path, the predicted ablation area, the probe marker for planning and the area of tissue to be ablated, may be saved. Every time they are saved, one ablation needle plan is completed, where the completed ablation needle plan may be used in subsequent guidance phase. After completing the planning of one ablation needle, when an instruction for setting another needle insertion path is received, the predicted ablation areas of the completed ablation needle plans may be displayed on the planning image so as to assist the user to perform the planning of the current ablation needle. In one embodiment, in the display method, the real-time planning coverage may also be calculated and displayed, where the real-time planning coverage=((the volume of the predicted ablation areas of the saved ablation needle plans U the volume of the current real-time predicted ablation area) ∩ the volume of the area of tissue to be ablated)/the volume of the area of tissue to be ablated. When the real-time planning coverage rate is 100%, it means that the area of tissue to be ablated is completely covered by the predicted ablation areas.

Figure 6:
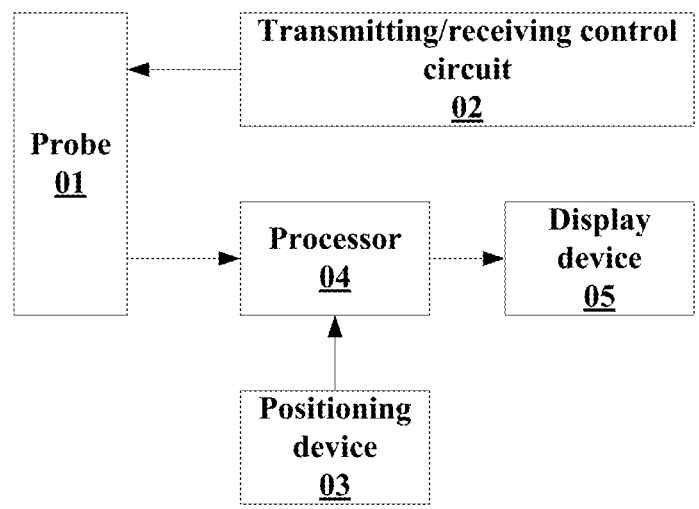
FIG. 6 is a schematic block diagram of a display system for ultrasound-guided intervention in one embodiment.

Referring to FIG. 6, a display system for ultrasound-guided intervention is also be provided in the present embodiment, which may include a probe 01, a transmitting/receiving control circuit 02, a positioning device 03, a processor 04 and a display device 05, which will be described in detail below.

The probe 01 may include transducers for converting between electrical energy and acoustic energy, which may be configured to transmit and receive ultrasonic waves.

The transmitting/receiving control circuit 02 may be configured to control the probe 01 to scan the tissue to obtain the ultrasound data in real time.

The positioning device 03 may be configured to obtain the spatial orientation information of the probe 01 in real time. The positioning device 03 may be an orientation sensor, a magnetic navigation system or other device which is able to obtain the spatial orientation information of the probe 01. The spatial orientation information of the probe 01 here may include the location information and the direction information of the probe 01.

The processor 04 may be configured to generate a planning image of the ultrasound-guided intervention based on the obtained data. The planning image may include a probe marker for planning, an ultrasound image and an area of tissue to be ablated. The planning image may at least represent the relative spatial position relationship between the probe marker for planning, the ultrasound image and the area of tissue to be ablated. In one embodiment, the processor 04 may be configured to generate the ultrasound image in real time according to the real-time ultrasound data. The processor 04 may be configured to obtain the area of tissue to be ablated according to the obtained data, where the area of tissue to be ablated may be able to be displayed in a three-dimensional form in the planning image. The area of tissue to be ablated may be displayed in the planning image. The area of tissue to be ablated may be displayed in a single color, that is, it may only present the size and shape of the tissue to be ablated, but ignore the attributes such as the internal density and gray value of the tissue to be ablated, etc., because in the planning image what are concerned may be the relative spatial position relationship between the probe marker for planning, the ultrasound image and the area of tissue to be ablated such that the user can understand the relative spatial position relationship between the actual probe, the tissue area represented by the ultrasound image and the area of tissue to be ablated. In addition, a real-time two-dimensional image for observing the area of tissue to be ablated may also be generated and displayed. In actual applications, a typical tissue to be ablated may be a tumor.

The display device 05 may be configured to display the planning image of the ultrasound-guided intervention described above.

In one embodiment, the probe marker generated by the processor 04 and displayed by the display device may be generated and displayed in a form which is able to indicate one or more sides of the probe. When the probe marker indicates one side of the probe 01, said one side may be any one of the front side, the back side, the left side and the right side of the probe 01; when the probe marker indicates multiple sides of the probe 01, said multiple sides may be at least two of the front side, the back side, the left side and the right side of the probe 01, or at least two or three of the front side of the probe 01, the back side of the probe 01, the left side of the probe 01, the right side of the probe 01 and the transmitting side of the probe, where the "at least three sides" may include the transmitting side of the probe. The probe marker may be embodied in many specific forms. For example, in one embodiment, the probe marker generated by the processor 04 and displayed by the display device 05 may include one or multiple linear objects. The number of the linear objects may be equal to the number of the sides of probe 01 to be indicated by the probe marker, and each linear object may indicate one side of the probe 01. In the case that there are multiple linear objects, the linear objects may be different in a first-type attribute. The first-type attribute may include the color, the length and/or the thickness. Alternatively, different marks may be marked on the linear objects. The marks may include the Chinese abbreviation or the English initial of the side of the probe 01 indicated by the linear object. For example, in one embodiment, the probe marker generated by the processor 04 and displayed by the display device 05 may include a probe model and one or multiple arrows arranged around the probe model, and each arrow may indicate one side of the probe. In the case that there are multiple arrows, the arrows may be different in a first-type attribute. The first-type attribute may include the color, the length and/or the thickness. Alternatively, different marks may be marked on the arrows. The marks may include the Chinese abbreviation or the English initial of the side of the probe 01 indicated by the arrow.

In one embodiment, when the probe is moved, the planning image may also be updated accordingly. The update of the planning image may include update of the spatial orientation of the probe marker for planning, the spatial position of the ultrasound image and the image content of the ultrasound image in the planning image.

Through the display system for ultrasound-guided intervention in the present embodiment, the planning image may be generated and displayed, which may be used to assist the user in preoperative planning. When performing a planning, the user can set the needle insertion path and the ablation parameters on the planning image according to the content of the planning image. For example, in one embodiment, the display system for ultrasound-guided intervention may further include a human-computer interaction unit, which may be a screen with a touch screen function, a mouse or a keyboard, etc. The processor 04 may be configured to receive instructions through the human-computer interaction unit. For example, the processor 04 may be configured to receive an instruction for setting the needle insertion path and an instruction for setting the ablation parameters, and generate the needle insertion path of the ablation needle and the predicted ablation area on the planning image according to the two instructions. In the case that the area of tissue to be ablated displayed on the planning image is three-dimensional, the generated and displayed predicted ablation area may also be three-dimensional. When the instruction for setting the needle insertion path or the instruction for setting the ablation parameter is updated, the needle insertion path or the predicted ablation area generated on the planning image may also be updated accordingly. In one embodiment, the needle insertion path may be shown by a solid line, a dashed line or a line with an arrow, etc. in a certain color. By the needle insertion path on the planning image, the user can clearly observe the organs and tissues to be punctured by the ablation needle when the ablation needle is inserted along the needle insertion path. Therefore, the accidental injury to important organs and blood vessels and the influence of ribs to the needle insertion path can be avoided during the planning of the needle insertion path. The predicted ablation area may simulate the predicted ablation range under the set needle insertion path and the set ablation parameter. Since the actual ablation range is usually ellipsoidal, in one embodiment, a three-dimensional ellipsoid may be used to represent the predicted ablation arrange. The transparency of the predicted ablation range displayed on the planning image may be adjustable, so as to facilitate the observation of the overlap between the predicted ablation area and the area of tissue to be ablated. When the predicted ablation area completely covers the area of tissue to be ablated, it means that the area of tissue to be ablated will be completely ablated. It should be noted that when only one ablation needle is set, one predicted ablation area may completely cover the area of tissue to be ablated; when multiple ablation needle are set, multiple predicted ablation areas may together completely cover the area of tissue to be ablated. In one embodiment, the predicted ablation area and the area of tissue to be ablated may be displayed in different colors, so as to facilitate the user to observe the predicted ablation of the area of tissue to be ablated. Therefore, it will be easy to observe the small areas which will be prone to be missed when observed in traditional two-dimensional images layer by layer, thereby effectively improving the success rate of ablation surgery.

When the processor 04 receives the save instruction, at least the current needle insertion path, the predicted ablation area, the probe marker for planning and the ablation parameters on the current planning image, as well as the relative spatial position relationship between the needle insertion path, the predicted ablation area, the probe marker for planning and the area of tissue to be ablated, may be saved. Every time they are saved, one ablation needle plan is completed, where the completed ablation needle plan may be used in subsequent guidance phase. After completing the planning of one ablation needle, when the processor 04 further receives an instruction for setting another needle insertion path, the predicted ablation areas of the completed ablation needle plans may be displayed on the planning image so as to assist the user to perform the planning of the current ablation needle. In one embodiment, the processor 04 may further be configured to calculate, and display through the display device 05, the real-time planning coverage, where the real-time planning coverage=((the volume of the predicted ablation areas of the saved ablation needle plans U the volume of the current real-time predicted ablation area) CI the volume of the area of tissue to be ablated)/the volume of the area of tissue to be ablated. When the real-time planning coverage rate is 100%, it means that the area of tissue to be ablated is completely covered by the predicted ablation areas.

With the display method and system for ultrasound-guided intervention provided in the present embodiment, the planning image may be generated and displayed, by which the user can conveniently view the area of tissue to be ablated, the relative spatial positions of the ultrasound image and the area of tissue to be ablated, the needle insertion path and the predicted ablation area during preoperative planning. It not only provides a more intuitive display effect, but also provide the relative spatial positional relationship between the probe, the area of tissue to be ablated, the ultrasound image, the needle insertion path and the predicted ablation area, which can help the user to quickly and accurately locate the area of tissue to be ablated and complete the preoperative planning to make an interventional surgery plan. For example, after the planning image is generated and displayed, when the user moves the actual probe, the spatial position of the probe marker, the spatial position of the ultrasound image and the content of the ultrasound image will change accordingly. The user may move the actual probe such that the area of tissue to be ablated is located in the ultrasound image. At this time, the user may also observe the real-time two-dimensional image of the area of tissue to be ablated in another window. When starting the planning, the user may move the probe and observe the relative positions of the probe marker, the ultrasound image and the area of tissue to be ablated to find a better needle insertion path and set better ablation parameters, and then save the current ablation needle plan, thereby completing one ablation needle plan. When it is necessary to make multiple ablation needle plans, the user can also view the current coverage of the area of tissue to be ablated through the real-time planning coverage so as to avoid the missing of small areas, ensure that the area of tissue to be ablated can be predicted to be completely ablated and maximize the first-time success rate of the ablation of the area of tissue to be ablated.

The display methods for ultrasound-guided intervention in the embodiments above are mainly display methods in the planning stage. In the present embodiment, display methods for ultrasound-guided intervention may also be provided, which are mainly display methods in the guidance stage.

Referring to FIG. 7, the display method for ultrasound-guided intervention provided in the present embodiment may include step S20 and step S22, which will be described in detail below.

In step S20, data may be obtained. The data may at least include real-time ultrasound data and real-time spatial orientation information of the probe. The real-time ultrasound data may be two-dimensional or three-dimensional ultrasound data obtained by scanning the tissue by the probe, or other suitable real-time data representing the tissue. The real-time spatial orientation information of the probe may be obtained by a positioning device, such as an orientation sensor, etc. The real-time spatial orientation information may include the location information of the probe and the direction information of the probe.

In step S22, a guiding image for ultrasound-guided intervention may be generated and displayed according to the obtained data and the pre-saved ablation needle plan obtained. The guiding image may include the probe marker for planning, a probe marker for guiding, the ultrasound image and the area of tissue to be ablated. The guiding image may be used to at least represent the relative spatial position relationship between the probe marker for planning, the probe marker for guiding, the ultrasound image and the area of tissue to be ablated. In step S22, the pre-saved ablation needle plan and the probe marker for planning may be the ablation needle plan and the probe marker for planning described above. In one embodiment, in step S22, the ultrasound image may be generated according to the real time ultrasound data and displayed in real time; the area of tissue to be ablated may be obtained according to the obtained data, where the area of tissue to be ablated may be able to be displayed in a three-dimensional form in the planning image; and the area of tissue to be ablated may be displayed in the guiding image. The area of tissue to be ablated may be displayed in a single color, that is, it may only present the size and shape of the tissue to be ablated, but ignore the attributes such as the internal density and gray value of the tissue to be ablated, etc., because in the guiding image what are concerned may be the relative spatial position relationship between the probe marker for planning, the probe marker for guiding, the ultrasound image and the area of tissue to be ablated such that the user can understand the relative spatial position relationship between the actual probe, the tissue area represented by the ultrasound image and the area of tissue to be ablated, and the position relationship between the probe marker for planning and the probe marker for guiding. In addition, a real-time two-dimensional image for observing the area of tissue to be ablated may also be generated and displayed. In actual applications, a typical tissue to be ablated may be a tumor.

In the guiding image, the probe marker for planning may be that in the pre-saved ablation needle plan, and may represent the spatial orientation of the probe saved in the planning stage. The probe marker for guiding may be generated according to the real-time spatial orientation information of the probe, and represent the actual spatial orientation of the probe in the guiding phase. When the probe is moved, the spatial orientation of the probe marker for guiding will change accordingly. In the guiding image, the probe marker for planning may be used to assist the user to make the probe marker for guiding to be coincided with the probe marker for planning by moving the probe. When the user moves the probe to cause the probe marker for guiding being coincided with the probe marker for planning, the user can accurately determine the needle insertion path in the ablation needle plan corresponding to the probe marker for planning according to the actual spatial position of the probe, and then perform the needle insertion and ablation.

In one embodiment, in order to make it easier for the user to move the probe to make the probe marker for guiding to be coincided with the probe marker for planning, the probe marker (including the probe marker for guiding and the probe marker for planning) in the guiding image may be generated and displayed in a form that can indicate one or more sides of the probe such that the orientation of the probe marker for guiding determined and updated according to the real-time spatial orientation information of the probe represents the orientation of the probe, so as to assist the user to coincide the probe marker for guiding with the probe marker for planning by moving the probe to cause the orientation of the probe marker for guiding to be same with the orientation of the probe marker for planning. The orientation of the probe marker for guiding may include the location of the probe marker for guiding and the direction of the probe marker for guiding. The location of the probe marker for guiding may be determined and updated according to the location information of the probe, and the direction of the probe marker for guiding may be determined and updated according to the direction information of the probe.

The probe marker for guiding and the probe marker for planning may use the same marker. When the probe marker is generated and displayed in a form that can indicate one side of the probe, said one side may be any one of the front side, the back side, the left side and the right side of the probe; when the probe marker is generated and displayed in a form that can indicate multiple sides of the probe, said multiple sides may be at least two of the front side, the back side, the left side and the right side of the probe, or at least two or three of the front side of the probe, the back side of the probe, the left side of the probe, the right side of the probe and the transmitting side of the probe, where the "at least three sides" may include the transmitting side of the probe. The probe marker may be embodied in many specific forms. For example, in one embodiment, the probe marker may include one or multiple linear objects. The number of the linear objects may be equal to the number of the sides of probe to be indicated by the probe marker, and each linear object may indicate one side of the probe. In the case that there are multiple linear objects, the linear objects may be different in the first-type attribute. The first-type attribute may include the color, the length and/or the thickness. Alternatively, different marks may be marked on the linear objects. The marks may include the Chinese abbreviation or the English initial of the side of the probe indicated by the linear object. FIG. 2 shows a probe marker, which has been described above and will not be described again. The probe marker may also be in other forms. For example, in one embodiment, the probe marker may include a probe model and one or multiple arrows arranged around the probe model, and each arrow may indicate one side of the probe. In the case that there are multiple arrows, the arrows may be different in a first-type attribute. The first-type attribute may include the color, the length and/or the thickness. Alternatively, different marks may be marked on the arrows. The marks may include the Chinese abbreviation or the English initial of the side of the probe indicated by the arrow. In one embodiment, the size of the probe marker may be zoomed in or out according to user needs, or be set to an initial default value. The probe marker provided in the present embodiment is very visually intuitive. Furthermore, because the probe marker itself can represent the direction of the probe by indicating the one or multiple sides thereof, the spatial orientation of the probe relative to the area of tissue to be ablated and the current placement state of the probe (such as the direction of the probe and the location of the probe) can be clearly displayed by the guiding image. Furthermore, since the probe marker can represent the orientations of the probe, the user can move the probe with reference to the orientation of the probe represented by the probe marker so as to make the probe marker for guiding to coincide with the probe marker for planning.

When the probe is moved, the guiding image may also be updated accordingly. The update of the guiding image may include update of the spatial orientation of the probe marker for guiding, the spatial position of the ultrasound image and the image content of the ultrasound image in the guiding image.

During the user moving the probe to make the probe marker for guiding to coincide with the probe marker for planning, the spatial position of the probe marker for guiding will change due to the movement of the probe. Therefore, the probe marker for guiding and the probe marker for planning can be distinguished. In one embodiment, in order to further distinguish the probe marker for guiding from the probe marker for planning, the probe marker for planning and the probe marker for guiding may be different in a second-type attribute. The second-type attribute may include the brightness and/or transparency, etc. Alternatively, different marks may be marked on the probe marker for planning and the probe marker for guiding. For example, the probe marker for planning may be marked with the text "Planning", the probe for guiding may be marked with the text "Guiding", and so on.

The guiding image in step S22 may be generated based on the data obtained in step S20 and the pre-saved ablation needle plan. In some cases, multiple ablation needle plans may be saved in the planning stage, and it may be necessary to determine which ablation needle plan will be used to generate the guiding images and perform the ablation surgery. Therefore, in one embodiment, the display method for ultrasound-guided intervention may further include a step of receiving a user's instruction for select the ablation needle plan. For example, this step may include receiving a selection instruction and calling the ablation needle plan for generating the guiding image according to the selection instruction. The guiding image may further include the needle insertion path and the predicted ablation area in the called ablation needle plan, where the relative spatial position between the needle insertion path, the predicted ablation area, the probe marker for planning and the area of tissue to be ablated in the guiding image may be fixed. When a new selection instruction is received, the corresponding ablation needle plan may be called according to the new selection instruction, and the needle insertion path, the predicted ablation area and the probe marker for planning in the guiding image may be updated. The ablation needle plan and the probe marker planning in the present embodiment may be the ablation needle plan and the probe marker planning provided in the embodiment above, and the display form of the needle insertion path and the predicted ablation area in the guiding image may be similar to the needle insertion path and the predicted ablation area in the planning image of the embodiment above, which will not be described here again.

In one embodiment, the display method for ultrasound-guided intervention may further include calculating and displaying a real-time guiding coverage and/or a coincidence rate. The real-time guiding coverage=(((the volume of the predicted ablation area in the saved ablation needle plan−the volume of the predicted ablation area in the currently selected ablation needle plane) ∪ the volume of the current real-time predicted ablation area) ∩ the volume of the area of tissue to be ablated)/the volume of the area of tissue to be ablated. The coincidence rate=(the volume of predicted ablation area in the currently selected ablation needle plan ∩ the volume of the current real-time predicted ablation area)/the volume of the predicted ablation area in the currently selected ablation needle plan. Calculating and displaying the real-time guiding coverage and/or the coincidence rate can help the user to determine the coincidence between the probe marker for guiding and the probe marker for planning and the coverage of the real-time predicted ablation area to the area of tissue to be ablated.

Through the steps above, the guiding image may be generated and displayed. The guiding image may be used to assist the user in guiding the needle during the operation. For example, FIG. 8 shows a guiding image in which the probe marker is in the form shown in FIG. 2. The user can move the probe to make the probe marker for guiding to coincide with the probe marker for planning, and then perform the subsequent needle insertion to perform the ablation.

Figure 9:
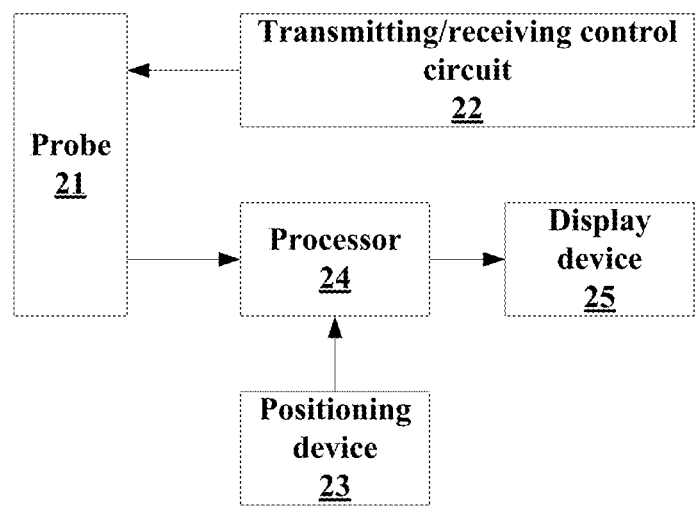
FIG. 9 is a schematic block diagram of a display system for ultrasound-guided intervention in another embodiment.

Referring to FIG. 9, a display system for ultrasound-guided intervention may further be provided in the present embodiment. The display system for ultrasound-guided intervention may include a probe 21, a transmitting/receiving control circuit 22, a positioning device 23, a processor 24 and a display device 25, which will be described in detail below.

The probe 21 may include transducers for converting between electrical energy and acoustic energy, which may be configured to transmit and receive ultrasonic waves.

The transmitting/receiving control circuit 22 may be configured to control the probe 21 to scan the tissue to obtain the ultrasound data in real time.

The positioning device 23 may be configured to obtain the spatial orientation information of the probe 21 in real time. The positioning device 23 may be an orientation sensor, a magnetic navigation system or other device which is able to obtain the spatial orientation information of the probe 21. The spatial orientation information of the probe 21 here may include the location information and the direction information of the probe 21.

The processor 24 may be configured to generate the guiding image for ultrasound-guided intervention according to the data obtained by the probe 21 and the pre-saved ablation needle plan. The guiding image may include the probe marker for planning, the probe marker for guiding, the ultrasound image and the area of tissue to be ablated. The guiding image may be used to at least represent the relative spatial position relationship between the probe marker for planning, the probe marker for guiding, the ultrasound image and the area of tissue to be ablated. The pre-saved ablation needle plan and the probe marker for planning may be the ablation needle plan and the probe marker for planning described above. In one embodiment, the processor 24 may generate the ultrasound image in real time according to the real time ultrasound data; obtain the area of tissue to be ablated according to the obtained three-dimensional data, where the area of tissue to be ablated may be able to be displayed in a three-dimensional form in the guiding image; and display the area of tissue to be ablated in the guiding image. The area of tissue to be ablated may be displayed in a single color, that is, it may only present the size and shape of the tissue to be ablated, but ignore the attributes such as the internal density and gray value of the tissue to be ablated, etc., because in the guiding image what are concerned may be the relative spatial position relationship between the probe marker for planning, the probe marker for guiding, the ultrasound image and the area of tissue to be ablated such that the user can understand the relative spatial position relationship between the actual probe, the tissue area represented by the ultrasound image and the area of tissue to be ablated, and the position relationship between the probe marker for planning and the probe marker for guiding. In addition, a real-time two-dimensional image for observing the area of tissue to be ablated may also be generated and displayed. In actual applications, a typical tissue to be ablated may be a tumor.

The display device 25 may be configured to display the planning image of the ultrasound-guided intervention described above.

In one embodiment, in the guiding image generated by the processor 24 and displayed by the display device 25, the probe marker for planning may be generated according to the pre-saved ablation needle plan, and may represent the spatial position of the probe saved in the planning stage. The probe marker for guiding may be generated according to the real-time spatial orientation information of the probe, and represent the actual spatial position of the probe in the guiding phase. When the probe is moved, the spatial position of the probe marker for guiding will change accordingly. In the guiding image, the probe marker for planning may be used to assist the user to make the probe marker for guiding to be coincided with the probe marker for planning by moving the probe. When the user moves the probe to cause the probe marker for guiding being coincided with the probe marker for planning, the user can accurately determine the needle insertion path in the ablation needle plan corresponding to the probe marker for planning according to the actual spatial position of the probe, and then perform the needle insertion and ablation. In one embodiment, in order to make it easier for the user to move the probe to make the probe marker for guiding to be coincided with the probe marker for planning, the probe marker (including the probe marker for guiding and the probe marker for planning) in the guiding image may be generated and displayed in a form that can indicate one or more sides of the probe. The probe marker for guiding and the probe marker for planning may use the same marker. When the probe marker is generated and displayed in a form that can indicate one side of the probe, said one side may be any one of the front side, the back side, the left side and the right side of the probe; when the probe marker is generated and displayed in a form that can indicate multiple sides of the probe, said multiple sides may be at least two of the front side, the back side, the left side and the right side of the probe, or at least two or three of the front side of the probe, the back side of the probe, the left side of the probe, the right side of the probe and the transmitting side of the probe, where the "at least three sides" may include the transmitting side of the probe. The probe marker may be embodied in many specific forms. For example, in one embodiment, the probe marker may include one or multiple linear objects. The number of the linear objects may be equal to the number of the sides of probe to be indicated by the probe marker, and each linear object may indicate one side of the probe. In the case that there are multiple linear objects, the linear objects may be different in the first-type attribute. The first-type attribute may include the color, the length and/or the thickness. Alternatively, different marks may be marked on the linear objects. The marks may include the Chinese abbreviation or the English initial of the side of the probe indicated by the linear object. FIG. 2 shows a probe marker, which has been described above and will not be described again. The probe marker may also be in other forms. For example, in one embodiment, the probe marker may include a probe model and one or multiple arrows arranged around the probe model, and each arrow may indicate one side of the probe. In the case that there are multiple arrows, the arrows may be different in a first-type attribute. The first-type attribute may include the color, the length and/or the thickness. Alternatively, different marks may be marked on the arrows. The marks may include the Chinese abbreviation or the English initial of the side of the probe indicated by the arrow. In one embodiment, the size of the probe marker may be zoomed in or out according to user needs, or be set to an initial default value. The probe marker provided in the present embodiment is very visually intuitive. Furthermore, because the probe marker itself can represent the direction of the probe by indicating the one or multiple sides of the probe, the spatial position of the probe relative to the area of tissue to be ablated and the current placement state of the probe (such as the direction of the probe and the location of the probe) can be clearly displayed by the guiding image. Furthermore, since the probe marker can represent the orientations of the probe, the user can move the probe with reference to the orientation of the probe represented by the probe marker so as to make the probe marker for guiding to coincide with the probe marker for planning.

In one embodiment, when the probe is moved, the guiding image may also be updated accordingly. The update of the guiding image may include update of the spatial orientation of the probe marker for guiding, the spatial position of the ultrasound image and the image content of the ultrasound image in the guiding image.

During the user moving the probe 21 to make the probe marker for guiding to coincide with the probe marker for planning, the spatial position of the probe marker for guiding will change due to the movement of the probe 21. Therefore, the probe marker for guiding and the probe marker for planning can be distinguished. In one embodiment, in order to further distinguish the probe marker for guiding from the probe marker for planning, the processor 21 may set the probe marker for planning and the probe marker for guiding with different second-type attribute. The second-type attribute may include the brightness and/or transparency, etc. Alternatively, the processor may mark the probe marker for planning and the probe marker for guiding with different marks. For example, the probe marker for planning may be marked with the text "Planning", the probe for guiding may be marked with the text "Guiding", and so on.

The guiding image generated by the processor 24 may be generated based on the data obtained by the probe 21 and the positioning device 23 and the pre-saved ablation needle plan. In some cases, multiple ablation needle plans may be saved in the planning stage, and it may be necessary to determine which ablation needle plan will be used to generate the guiding image and perform the ablation surgery. Therefore, in one embodiment, the display system for ultrasound-guided intervention may further include a human-computer interaction unit. The processor 24 may receive instructions through the human-computer interaction unit. For example, the processor 24 may receive the selection instruction through the human-computer interaction unit, and call the ablation needle plan for generating the guiding image according to the selection instruction. The guiding image may further include the needle insertion path and the predicted ablation area in the called ablation needle plan, where the relative spatial position between the needle insertion path, the predicted ablation area, the probe marker for planning and the area of tissue to be ablated in the guiding image may be fixed. When a new selection instruction is received, the corresponding ablation needle plan may be called according to the new selection instruction, and the needle insertion path, the predicted ablation area and the probe marker for planning in the guiding image may be updated accordingly. The ablation needle plan and the probe marker planning in the present embodiment may be the ablation needle plan and the probe marker planning provided in the embodiment above, and the display form of the needle insertion path and the predicted ablation area in the guiding image may be similar to the needle insertion path and the predicted ablation area in the planning image of the embodiment above, which will not be described here again.

In order to help the user to determine the coincidence between the probe marker for guiding and the probe marker for planning and the coverage of the real-time predicted ablation area to the area of tissue to be ablated, in one embodiment, the processor 24 may further calculate and display the real-time guiding coverage and/or the coincidence rate. The real-time guiding coverage=(((the volume of the predicted ablation area in the saved ablation needle plan–the volume of the predicted ablation area in the currently selected ablation needle plane) ∪ the volume of the current real-time predicted ablation area) ∩ the volume of the area of tissue to be ablated)/the volume of the area of tissue to be ablated. The coincidence rate=(the volume of predicted ablation area in the currently selected ablation needle plan ∩ the volume of the current real-time predicted ablation area)/the volume of the predicted ablation area in the currently selected ablation needle plan.

In the display methods and systems for ultrasound-guided intervention provided in the present disclosure, the guiding image may be generated and displayed, which may be used for assisting the user to perform the planned needle insertion and the ablation. For example, the guiding image may include the probe marker for planning and the probe marker for guiding. By moving the probe, the user can make the probe marker for guiding to coincide with the probe marker for planning. Therefore, the needle insertion path in the planning stage can be accurately located, so as to ensure the intervention accuracy as much as possible, avoid the incomplete ablation of the area of tissue to be ablated, and reduce the normal tissue damage.

Those skilled in the art can understand that all or part of the functions of the various methods in the embodiments described above may be implemented by hardware, or by a computer program. In the case that all or parts of the functions in the embodiments above are implemented by computer programs, the programs may be stored in a computer-readable storage medium. The storage medium may include a read-only memory, a random access memory, a magnetic disk, an optical disk, a hard disk or the like. The computer may execute the programs to implement the functions above. For example, the programs may be stored in the memory of the system. When the programs in the memory are executed by the processor, all or parts of the functions above can be implemented. In addition, in the case that all or parts of the functions in the embodiments above are implemented by computer programs, the programs may also be stored in a storage medium such as a server, another computer, a magnetic disk, an optical disk, a flash disk, a mobile hard disk or the like, and be saved to the memory of the local system by downloading or copying or by updating the version of the local system. When the programs in the memory are executed by the processor, all or parts of the functions in the embodiments above can be implemented.

The present disclosure has been described with reference to specific examples, which is only used to facilitate the understanding to the present disclosure, but not intended to limit the present disclosure. For those ordinarily skilled in the art, based on the concepts of the present disclosure, the specific embodiments above may be modified.

This disclosure has been made with reference to various exemplary embodiments. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. A display method for ultrasound-guided intervention, comprising:
   obtaining, via a probe, a data, wherein the data comprises at least a real-time ultrasound data and a real-time spatial orientation information of the probe;
   obtaining, by a processor, an ablation needle plan, wherein, the ablation needle plan comprises at least a probe marker for planning, a needle insertion path and a predicted ablation area corresponding to the needle insertion path, and the probe marker for planning is generated in a form that indicates one side or multiple sides of the probe such that an orientation of the probe marker for planning represents a planned orientation of the probe;
   generating, by the processor, a guiding image for ultrasound-guided intervention according to the obtained data and the ablation needle plan; and
   displaying, by a display device, the guiding image;
   wherein,
   the guiding image comprises the probe marker for planning, the needle insertion path, the predicted ablation area corresponding to the needle insertion path, a probe marker for guiding and an ultrasound image obtained according to the obtained real-time ultrasound data, and represents at least a relative spatial position relationship between the probe marker for planning, the probe marker for guiding, the ultrasound image and the predicted ablation area, wherein, the probe marker for guiding is generated in a form that indicates one side or multiple sides of the probe such that an orientation of the probe marker for guiding determined and updated according to the real-time spatial orientation information of the probe represents an orientation of the probe, and moving the probe marker for guiding when a user moves the probe, to cause the orientation of the probe marker for guiding to be same with the orientation of the probe marker for planning on the guiding image.

2. The display method of claim 1, wherein:
   the one side of the probe is any one of a front side of the probe, a back side of the probe, a left side of the probe and a right side of the probe; and
   the multiple sides of the probe are at least two of a front side of the probe, a back side of the probe, a left side of the probe and a right side of the probe, or are at least two or at least three of a front side of the probe, a back side of the probe, a left side of the probe, a right side of the probe and a transmitting side of the probe, wherein the at least three sides comprises the transmitting side of the probe.

3. The display method of claim 1, wherein:
   the probe marker for planning or the probe marker for guiding comprises one or multiple linear objects, wherein, a number of the linear objects is equal to a number of the sides of the probe to be indicated by the probe marker for planning or the probe marker for guiding, and each linear object indicates one side of the probe.

4. The display method of claim 3, wherein the probe marker for planning or the probe marker for guiding comprises multiple linear objects, and the linear objects are different in a first-type attribute, wherein
   the first-type attribute comprises a color, a length and/or a thickness; or
   different marks are marked on the linear objects, wherein each of the marks comprises a Chinese abbreviation or an English initial of a side of a probe indicated by a corresponding linear object.

5. The display method of claim 1, wherein, the probe marker for planning or the probe marker for guiding comprises a probe model and one or multiple arrows arranged around the probe model, and each arrow indicates one side of the probe.

6. The display method of claim 5, wherein, in the case that there are the probe marker for planning or the probe marker for guiding comprises multiple arrows, the arrows are different in a first-type attribute, wherein
   the first-type attribute comprises a color, a length and/or a thickness; or
   different marks are marked on the arrows, wherein each of the marks comprises a Chinese abbreviation or an English initial of a side of a probe indicated by a corresponding arrow.

7. The display method of claim 1, wherein the ablation needle plan further comprises a relative spatial position relationship between the probe marker for planning, the needle insertion path and the predicted ablation area.

8. The display method of claim 1, wherein:
   the probe marker for planning and the probe marker for guiding are different in a second-type attribute, wherein the second-type attribute comprises a brightness and/or a transparency; or
   different marks are marked on the probe marker for planning and the probe marker for guiding.

9. The display method of claim 1, wherein,
   the real-time spatial orientation information of the probe comprises a location information and a direction information of the probe;
   the orientation of the probe marker for guiding comprises a location of the probe marker for guiding and a direction of the probe marker for guiding; and
   the location of the probe marker for guiding is determined and updated according to the location information of the probe and the direction of the probe marker for guiding is determined and updated according to the direction information of the probe.

10. The display method of claim 9, wherein the orientation of the probe marker for planning comprises a location of the probe marker for planning and a direction of the probe marker for planning.

11. A display system for ultrasound-guided intervention, comprising:
    a probe;

a transmitting/receiving control circuit which is configured to control the probe to scan a tissue to obtain a real-time ultrasound data;

a positioning device which is configured to obtain a real-time spatial orientation information of the probe;

a processor which is configured to obtain an ablation needle plan and generate a guiding image for ultrasound-guided intervention according to the obtained real-time ultrasound data, the obtained real-time spatial orientation information of the probe and the obtained ablation needle plan; and a display device which is configured to display the guiding image;

wherein, the ablation needle plan comprises at least a probe marker for planning, a needle insertion path and a predicted ablation area corresponding to the needle insertion path, and the probe marker for planning is generated in a form that indicates one or multiple sides of the probe such that an orientation of the probe marker for planning represents an planned orientation of the probe; and the guiding image comprises the probe marker for planning, the needle insertion path, the predicted ablation area corresponding to the needle insertion path, a probe marker for guiding and an ultrasound image obtained according to the obtained real-time ultrasound data, and represents at least a relative spatial position relationship between the probe marker for planning, the probe marker for guiding, the ultrasound image and the predicted ablation area, wherein, the probe marker for guiding is generated in a form that indicates one or multiple sides of the probe such that an orientation of the probe marker for guiding determined and updated according to the real-time spatial orientation information of the probe represents an orientation of the probe, and moving the probe marker for guiding when a user moves the probe, to cause the orientation of the probe marker for guiding to be same with the orientation of the probe marker for planning on the guiding image.

12. The display system of claim 11, wherein:

the one side of the probe is any one of a front side of the probe, a back side of the probe, a left side of the probe and a right side of the probe; and the multiple sides of the probe are at least two of a front side of the probe, a back side of the probe, a left side of the probe and a right side of the probe, or are at least two or at least three of a front side of the probe, a back side of the probe, a left side of the probe, a right side of the probe and a transmitting side of the probe, wherein the at least three sides comprises the transmitting side of the probe.

13. The display system of claim 11, wherein:

the probe marker for planning or the probe marker for guiding comprises one or multiple linear objects, wherein, a number of the linear objects is equal to a number of the sides of the probe to be indicated by the probe marker for planning or the probe marker for guiding, and each linear object indicates one side of the probe.

14. The display system of claim 13, wherein the probe marker for planning or the probe marker for guiding comprises multiple linear objects, and the linear objects are different in a first-type attribute, wherein the first-type attribute comprises a color, a length and/or a thickness; or different marks are marked on the linear objects, wherein each of the marks comprises a Chinese abbreviation or an English initial of a side of a probe indicated by a corresponding linear object.

15. The display system of claim 11, wherein, the probe marker for planning or the probe marker for guiding comprises a probe model and one or multiple arrows arranged around the probe model, and each arrow indicates one side of the probe.

16. The display system of claim 15, wherein the probe marker for planning or the probe marker for guiding comprises multiple arrows, the arrows are different in a first-type attribute, wherein the first-type attribute comprises a color, a length and/or a thickness; or different marks are marked on the arrows, wherein each of the marks comprises a Chinese abbreviation or an English initial of a side of a probe indicated by a corresponding arrow.

17. The display system of claim 11, wherein, the ablation needle plan further comprises a relative spatial position relationship between the probe marker for planning, the needle insertion path and the predicted ablation area.

18. The display system of claim 11, wherein:

the probe marker for planning and the probe marker for guiding are different in a second-type attribute, wherein the second-type attribute comprises a brightness and/or a transparency; or different marks are marked on the probe marker for planning and the probe marker for guiding.

19. The display system of claim 11, wherein, the real-time spatial orientation information of the probe comprises a location information and a direction information of the probe;

the orientation of the probe marker for guiding comprises a location of the probe marker for guiding and a direction of the probe marker for guiding; and the location of the probe marker for guiding is determined and updated according to the location information of the probe and the direction of the probe marker for guiding is determined and updated according to the direction information of the probe.

20. The display system of claim 19, wherein the orientation of the probe marker for planning comprises a location of the probe marker for planning and a direction of the probe marker for planning.

* * * * *

UNITED STATES PATENT AND TRADEMARK OFFICE
CERTIFICATE OF CORRECTION

PATENT NO. : 12,144,554 B2
APPLICATION NO. : 16/991280
DATED : November 19, 2024
INVENTOR(S) : Yanhui Zhang et al.

Page 1 of 1

It is certified that error appears in the above-identified patent and that said Letters Patent is hereby corrected as shown below:

In the Claims

In Claim 6, Column 22, Line 28-29, "The display method of claim 5, wherein, in the case that there are the probe marker for planning" should read -- The display method of claim 5, wherein the probe marker for planning --

Signed and Sealed this
Eighteenth Day of February, 2025

Coke Morgan Stewart
*Acting Director of the United States Patent and Trademark Office*